United States Patent [19]

Grosso

[11] Patent Number: 5,162,543

[45] Date of Patent: Nov. 10, 1992

[54] SELECTIVE PROCESSES FOR FOSINOPRIL POLYMORPHS

[75] Inventor: John A. Grosso, Princeton Junction, N.J.

[73] Assignee: E. R. Squibb & Sons, Inc., Princeton, N.J.

[21] Appl. No.: 481,009

[22] Filed: Feb. 16, 1990

[51] Int. Cl.$^5$ .............................................. C07F 9/572
[52] U.S. Cl. ..................................................... 548/413
[58] Field of Search ........................................ 548/413

[56] References Cited

U.S. PATENT DOCUMENTS 4,337,201 6/1982 Petrillo, Jr. ........................ 548/513
4,734,508 3/1988 Thottathil .......................... 548/532

OTHER PUBLICATIONS

Morris et al., "Investigation of Polymorphism of Fosinopril Sodium . . . " presented at AAPS meeting, Oct. 1989.

Jerewski et al., "Identification and Physico-Chemical Characterization of Fosinopril . . . " presented at AAPS meeting in 1987.

*Primary Examiner*—Mark L. Berch
*Attorney, Agent, or Firm*—Timothy J. Gaul

[57] ABSTRACT

Described herein is a process for selectively preparing and interconverting polymorph salts of fosinopril, an antihypertensive agent that inhibits angiotensin converting enzyme. Each polymorph is prepared by mixing an alkali metal carrier, fosinopril, water and a keto and-/or hydroxylic solvent and isolating the polymorph formed from the reaction mixture. The less exothermic polymorph A is formed when the water makes up more than about 0.2% of the water and solvents; at about 0.2% or less, the more exothermic polymorph B is formed.

9 Claims, 5 Drawing Sheets

SELECTIVE PROCESSES FOR FOSINOPRIL POLYMORPHS

FIELD OF THE INVENTION

This invention relates to processes for the preparation and interconversion of polymorphs of fosinopril, an inhibitor of angiotensin converting enzyme (ACE) useful as an antihypertensive agent.

BACKGROUND OF THE INVENTION

U.S. Pat. No. 4,337,201 (issued Jun. 29, 1982) describes inter alia the compound

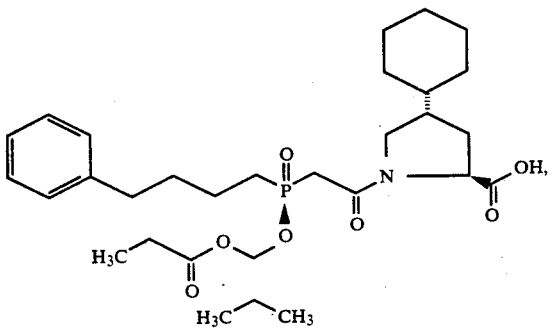

which has the generic name fosinopril and forms the alkali metal salt 1[S*(R*)],2α,4β]-4-cyclo-hexyl-1-[[[2-methyl-1-(1-oxopropoxy)propoxy](4-phenylbutyl)phosphinyl[acetyl]-L-proline, monosodium salt. Fosinopril and related compounds are ACE inhibitors having antihypertensive activity and other utilities as described in U.S. Pat. No. 4,337,201.

Figure 1:
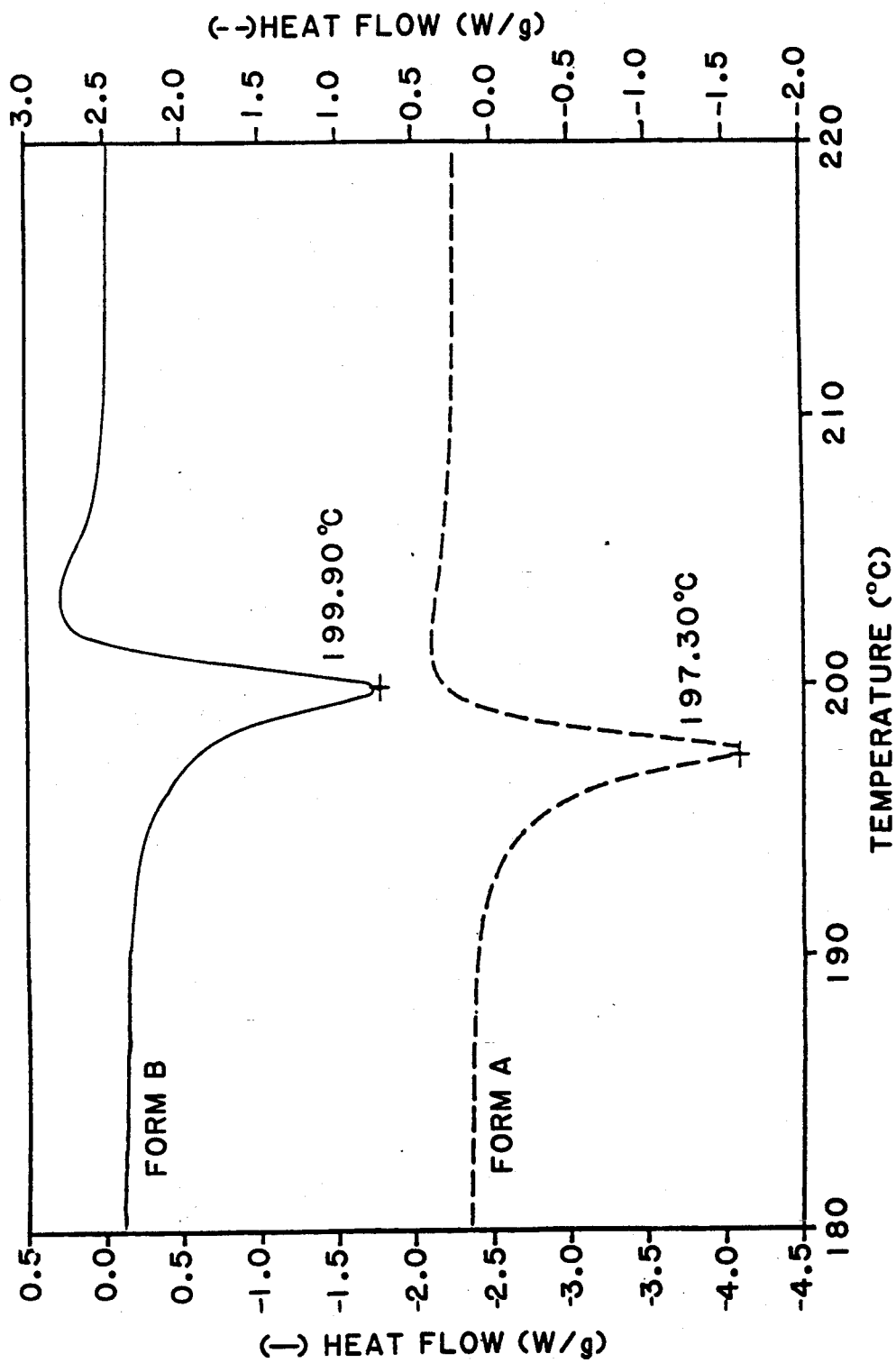
Figure 2:
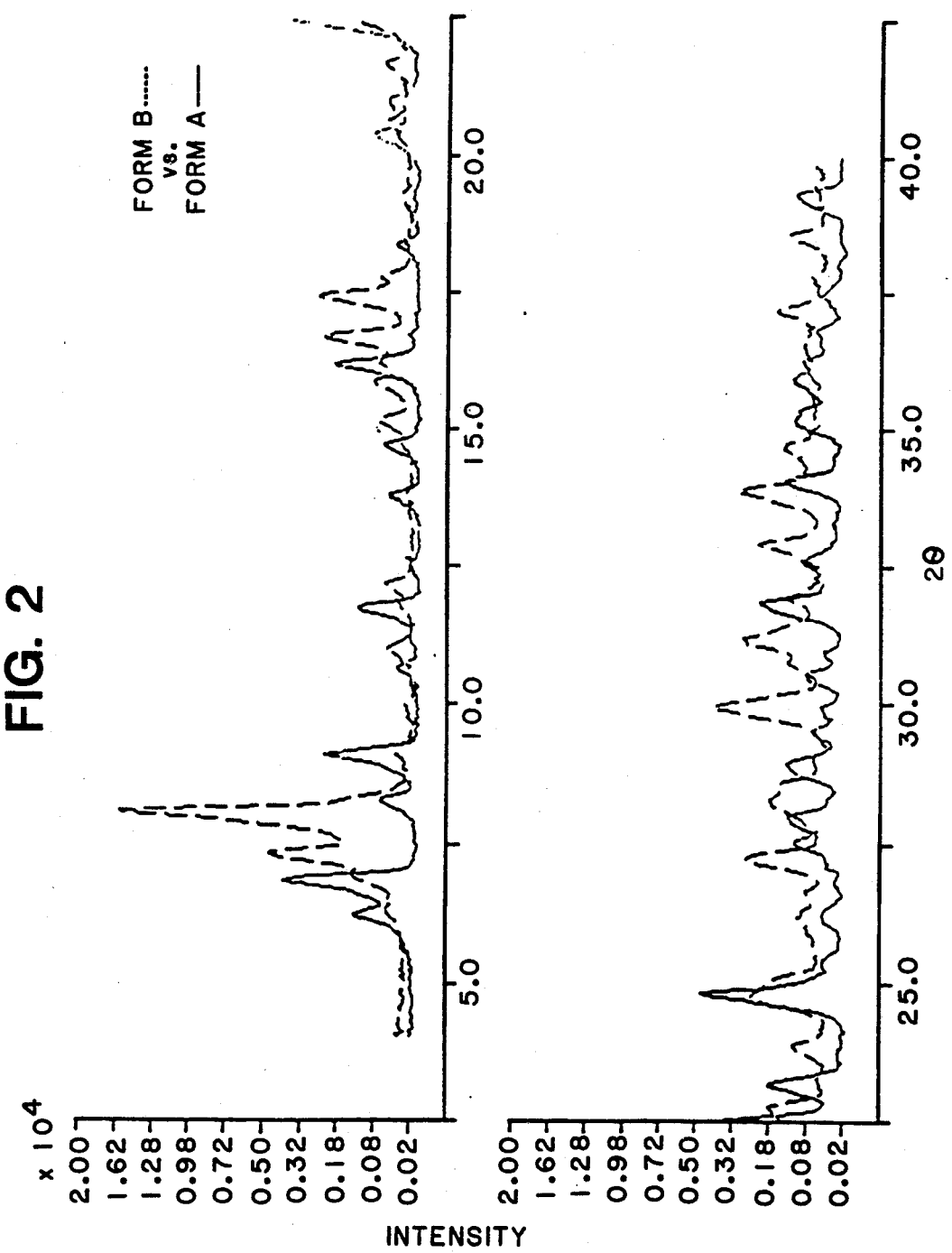
Figure 3A:
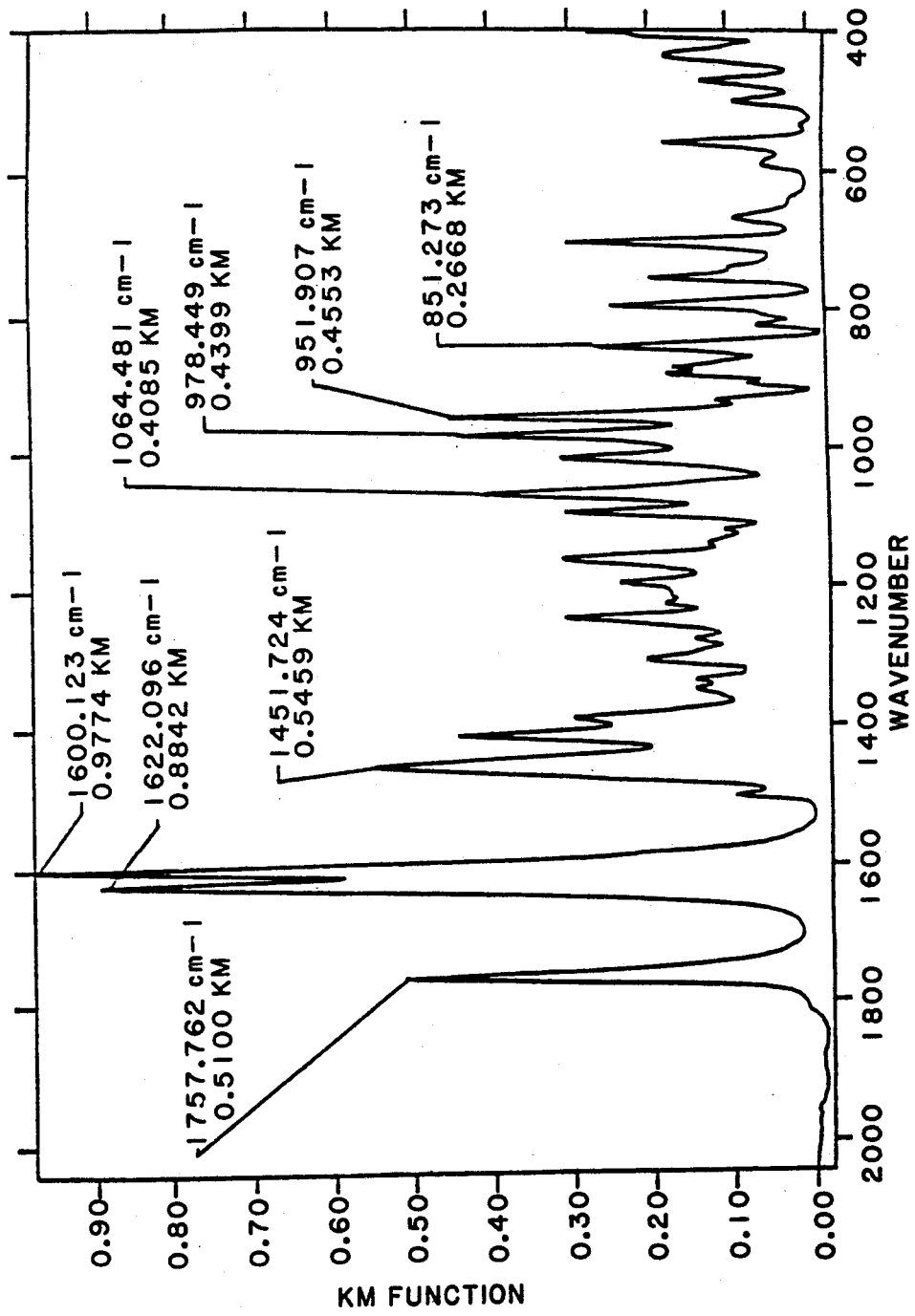
Figure 3B:
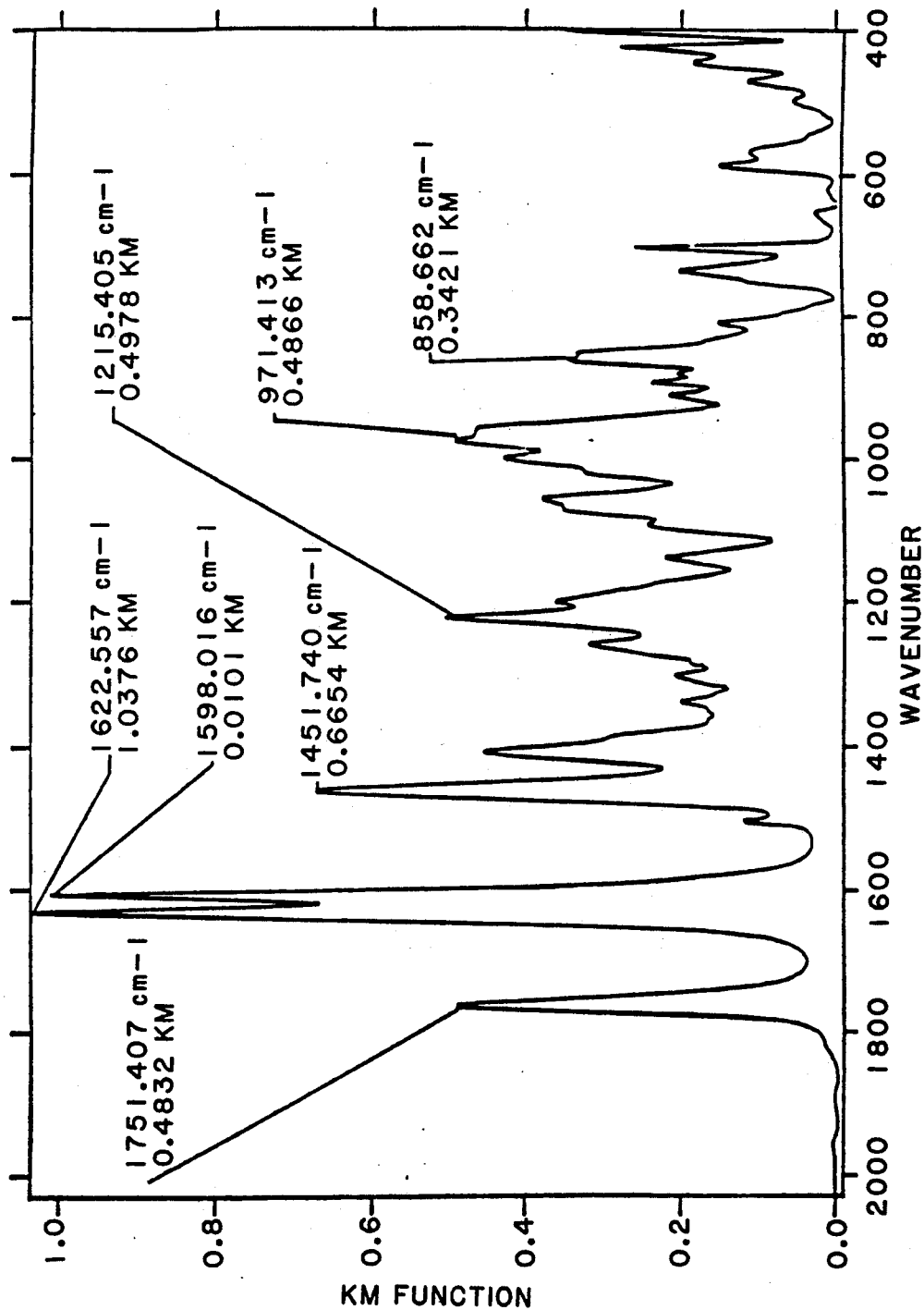
Figure 4:
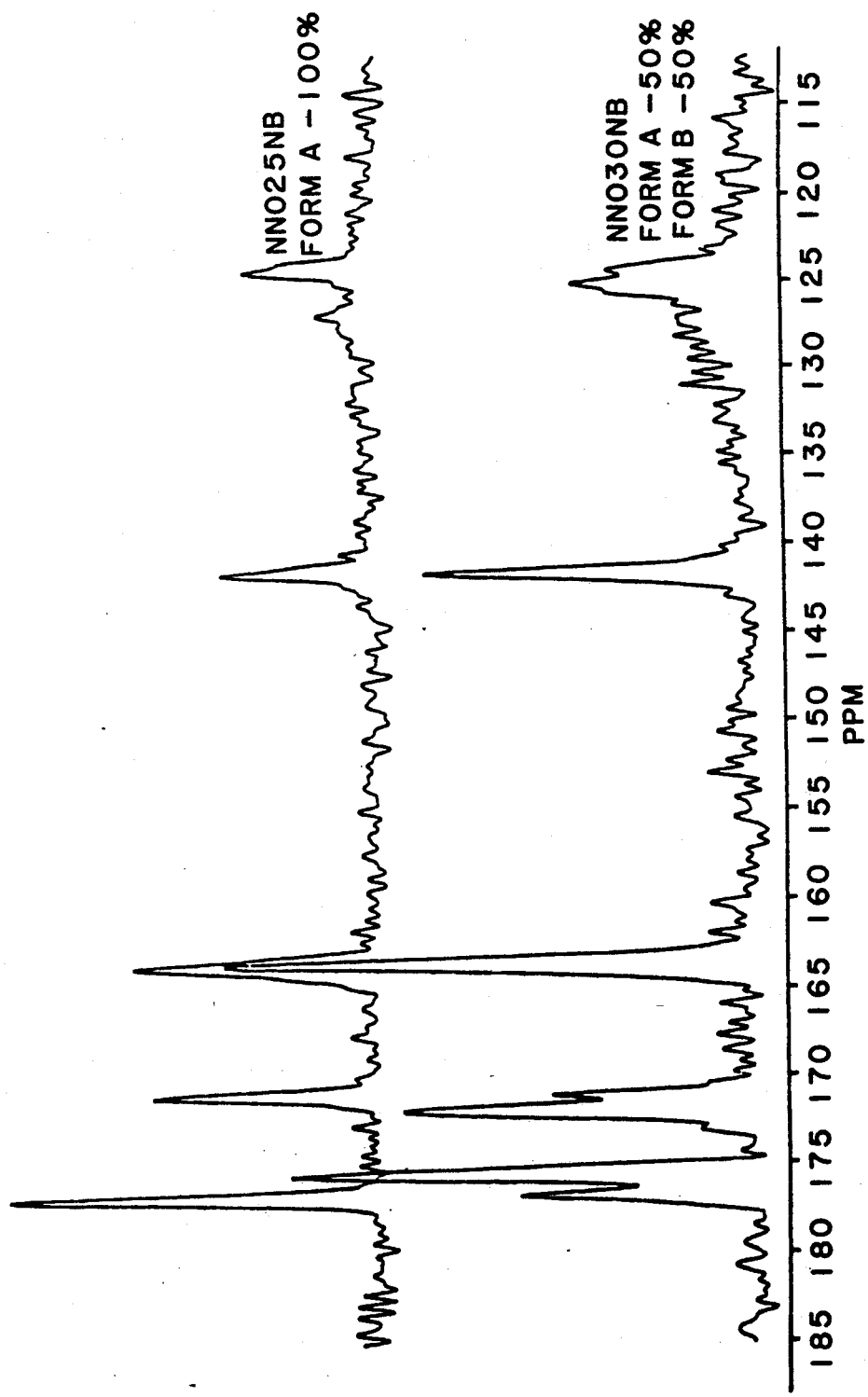

Calorimetric, spectroscopic, and other analyses have established that fosinopril sodium exists as two polymorphs, A and B (see FIGS. 1 to 4). FIG. 1 shows a differential scanning calorimetry thermogram of the two polymorphs. FIG. 2 shows powder X-ray diffraction spectra of the two polymorphs. FIGS. 3A and 3B show infrared diffuse reflectance spectra of the polymorphs. FIG. 4 shows carbon-13 NMR spectra of the two polymorphs. Polymorph B has been found to be much more exothermic than polymorph A upon dissolving, so that polymorph A is believed to be more thermodynamically stable (see Table 1, below).

TABLE 1

Heats of Solution of Two Different Polymorphs of Fosinopril Sodium

Form A: $\Delta H_S = -0.90$ Kcal/mole
Form B: $\Delta H_S = -2.46$ Kcal/mole

DESCRIPTION OF THE INVENTION

When fosinopril salt or fosinopril and an alkali metal carrier are placed in a keto or hydroxylic solvent or mixture thereof, the amount of water present determines which polymorph is formed. When the water comprises greater than about 0.2% of the amount of water and solvents added together, formation of polymorph A predominates. No water need be present for formation of polymorph B. When the water comprises about 0.2% or less of the amount of water and solvents added together, formation of polymorph B predominates. In either case, the polymorph formed crystallizes and is conventionally isolated from the solution.

In accordance with the present invention, a process is provided for preparing fosinopril-alkali metal salt polymorph A from either fosinopril (structure I) or polymorph B. In this process, either polymorph B or fosinopril and an alkali metal carrier are mixed with water and a keto or hydroxylic solvent or mixture thereof, after which polymorph A is isolated from the mixture. Water should be present in an amount greater than about 0.2% of the total amount of water and solvents added together. It is preferred that the amount of water present be limited, however, to minimize the amount of product lost to the mother liquor. Thus, it is preferred that the water comprise about 1 to 3% of the amount of water and solvents together.

Also in accordance with the present invention, a process is provided for preparing fosinopril-alkali metal salt polymorph B from fosinopril or polymorph A. In this process, polymorph A or fosinopril and an alkali metal carrier are mixed with a keto or hydroxylic solvent or mixture thereof having about 0.2 to 0% water (i.e., no water present), after which polymorph B is isolated from the mixture.

Further in accordance with the present invention, a process is provided for preparing polymorph B in which water is removed from a solution of (1) polymorph A or (2) fosinopril and an alkali metal carrier in a keto or hydroxylic solvent or mixture thereof and polymorph B is isolated from the solution. Removal of the water should be effected so that the amount of water is less than about 0.2% of the amount of the water and solvents together. Removal by vacuum concentration is preferred.

Throughout this specification, the term "alkali metal" refers to sodium (which is preferred), lithium, and potassium. Exemplary alkali metal carriers are sodium ethylhexanoate (which is preferred), potassium ethylhexanoate, lithium ethylhexanoate, and the like.

Exemplary keto solvents are acetone (which is preferred), methylethylketone, methylisobutylketone, and the like. Exemplary hydroxylic solvents are methanol (which is preferred), ethanol, isopropyl alcohol, and the like. Other solvents may be present but are not required.

The mixing step of the processes of the present invention may be accomplished by, for example, slurrying or stirring. Isolation may be accomplished by, for example, filtration of the reaction mixture. The invention will now be further described by the following working examples, which are preferred embodiments and are illustrative rather than limiting. All temperatures are in degrees Celsius.

EXAMPLE 1

Preparation of Fosinopril Sodium Polymorph A

A solution of 20.0 g of the cinchonidine salt, [R-(R*,S*)]-[[2-methyl-1-(1-oxopropoxy)-propoxy-(4-phenylbutyl)phosphinyl]acetic acid, cinchonidine salt (1:1) in 200 ml of methylene chloride was washed with three 200-ml portions of distilled water, each time adjusting the pH of the biphasic mixture to 2.0 with 6 N hydrochloric acid. Following the addition of 0.06 g of pyridine and 2.98 g of triethylamine, the solution was cooled to −10° C. To the cold solution was added 3.62 g pivaloyl chloride. The reaction mixture was stirred for 1 hour, followed by the addition of 6.88 g of (trans)-4-cyclohexyl-L-proline, monohydrochloride and 2.98 g of triethylamine. The mixture was then warmed to 25° C. and stirred for 90 minutes at that temperature. The product-rich solution was washed with three 200-ml portions of water, each time adjusting the pH of the biphasic mixture to 2.0 with 6 N hydrochloric acid. The organic layer was concentrated under vacuum to 21 g of an amber oil.

The oil was dissolved in 200 ml of acetone and 30.0 ml of 1 N sodium ethylhexanoate in acetone containing 13.56 percent water by volume. After stirring the crystal slurry for 6 hours at room temperature, the product was collected by filtration and washed on the filter with 70 ml of acetone. The wet cake was dried under vacuum, yielding 15.2 g (87.8 M%) of fosinopril sodium polymorph A.

EXAMPLE 2

Conversion of Polymorph B to Polymorph A

To a mixture of 490 ml of acetone and 10 ml of water was added 50.1 g of fosinopril sodium polymorph B. The slurry was stirred for 2 hours at room temperature and the product was isolated by filtration. Vacuum-drying afforded 49.5 g (99 M%) of fosinopril sodium polymorph A.

EXAMPLE 3

Conversion of Polymorph A to Polymorph B

To 15 ml of methanol was added 1.0 g of fosinopril sodium polymorph A. The resultant solution was vacuum-concentrated at 35° C. to dryness, yielding 1.0 g of fosinopril sodium polymorph B.

What is claimed is:

1. A process for preparing fosinopril salt polymorph A, which comprises:
    (a) mixing together
        (i) either (1) fosinopril salt or (2) fosinopril and an alkali metal carrier,
        (ii) a keto solvent or a hydroxylic solvent or a mixture thereof, and
        (iii) water, so that water comprises about 2% or more of the solvents; and
    (b) isolating polymorph A from the mixture.
2. The process of claim 1, wherein the alkali metal is sodium.
3. The process of claim 1, wherein a keto solvent is used to prepare polymorph A.
4. The process of claim 3, wherein the keto solvent is acetone.
5. A process for preparing fosinopril salt polymorph B, which comprises:
    (a) mixing together
        (i) either (1) fosinopril salt or (2) fosinopril and an alkali metal carrier,
        (ii) a keto solvent or a hydroxylic solvent or a mixture thereof, wherein water comprises about 0.2% or less of the solvents; and
    (b) isolating polymorph B from the mixture.
6. The process of claim 5, wherein a hydroxylic solvent is used to prepare polymorph B.
7. The process of claim 6, wherein the hydroxylic solvent is methanol.
8. The process of claim 1, wherein the alkali metal carrier is sodium ethylehexanoate.
9. The process of claim 5, wherein the water is removed by vacuum concentration.

* * * * *